US00PP25565P2

(12) United States Plant Patent
Zampini

(10) Patent No.: US PP25,565 P2
(45) Date of Patent: May 19, 2015

(54) ***PHILADELPHUS* PLANT NAMED 'ICEZAM'**

(50) Latin Name: *Philadelphus coronarius*
Varietal Denomination: Icezam

(71) Applicant: LCN Holdings, Inc., Perry, OH (US)

(72) Inventor: James W. Zampini, Madison, OH (US)

(73) Assignee: Lake Country Nursery, Perry, OH (US)

( * ) Notice: Subject to any disclaimer, the term of this patent is extended or adjusted under 35 U.S.C. 154(b) by 26 days.

(21) Appl. No.: 13/986,355

(22) Filed: Apr. 23, 2013

Related U.S. Application Data

(60) Provisional application No. 61/687,388, filed on Apr. 24, 2012.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of *Philadelphus coronaria*, 'Icezam', characterized by its foliage that is variegated with creamy white centers and light green margins, its upright and rounded plant habit, its small creamy white flowers and its moderate growth rate.

2 Drawing Sheets

Botanical classification: *Philadelphus coronarius*.
Variety denomination: 'Icezam'.

BACKGROUND OF THE INVENTION

The present invention relates to a new and distinct cultivar of *Philadelphus coronarius* and will be referred to hereafter by its cultivar name, 'Icezam'. 'Icezam' is a new cultivar of mock orange, a shrub grown for use as an ornamental landscape plant.

The new cultivar of *Philadelphus* was discovered as a naturally occurring whole plant mutation by the Inventor in Perry, Ohio in summer of 2008. The new cultivar was discovered growing in a seed bed that had been planted with seed derived from unnamed plants of *Philadelphus coronaria*. The exact parent plants are unknown.

Asexual reproduction of the new cultivar was first accomplished by the Inventor using softwood stem cuttings in summer of 2008 in Perry, Ohio. The characteristics of this cultivar have been determined to be stable and are reproduced true to type in successive generations.

SUMMARY OF THE INVENTION

The following traits have been repeatedly observed and represent the characteristics of the new cultivar as grown outdoors in Perry, Ohio. These attributes in combination distinguish 'Icezam' as a unique cultivar of *Philadelphus*.

1. 'Icezam' exhibits foliage that is variegated with green centers and creamy white margins.
2. 'Icezam' exhibits an upright and rounded plant habit.
3. 'Icezam' exhibits creamy white flowers that are smaller than is typical of plants of *Philadelphus coronarius*.
4. 'Icezam' exhibits a slower growth rate than is typical of plants of *Philadelphus coronarius*.

Typical plants of the *Philadelphus coronarius* differ from 'Icezam' in having a more vigorous growth habit, in having green non-variegated foliage, and in having larger flowers.

'Icezam' can be compared to the cultivars; 'Incsnozam' and 'Romanizam' selected by the same Inventor. 'Incsnozam' differs from 'Icezam' in having double flowers that are more fragrant and in having green non-variegated foliage with yellow fall color. 'Romanizam' differs from 'Icezam' in having flowers that are much larger and more fragrant and in having green non-variegated foliage. 'Icezam' can also be compared to the cultivar 'Variegatus' (not patented). 'Variegatus' is similar to 'Icezam' in having variegated foliage, however 'Variegatus' differs in having leaves with more variable variegation and in having more fragrant flowers.

BRIEF DESCRIPTION OF THE DRAWINGS

The accompanying colored photographs illustrate the overall appearance and distinct characteristics of the new *Philadelphus*. The photographs were taken of a two year-old plant as grown outdoors in trial garden in Perry, Ohio.

The photograph in FIG. 1 provides an overall view of the growth habit of 'Icezam'.

Figure 1:
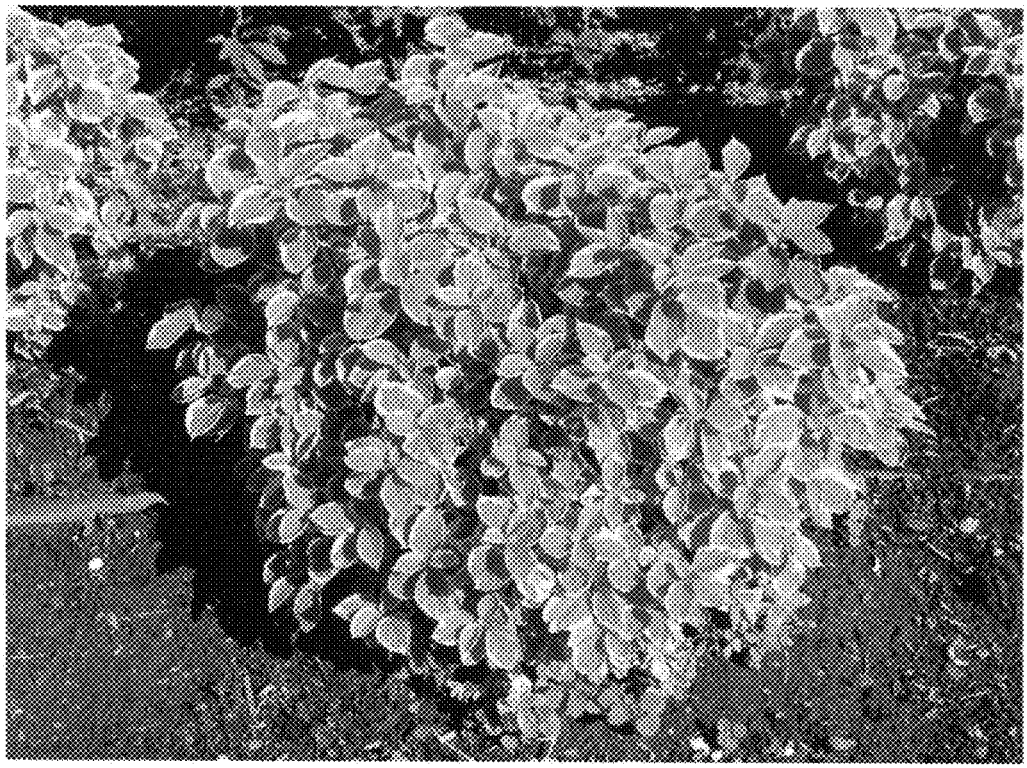
Figure 2:
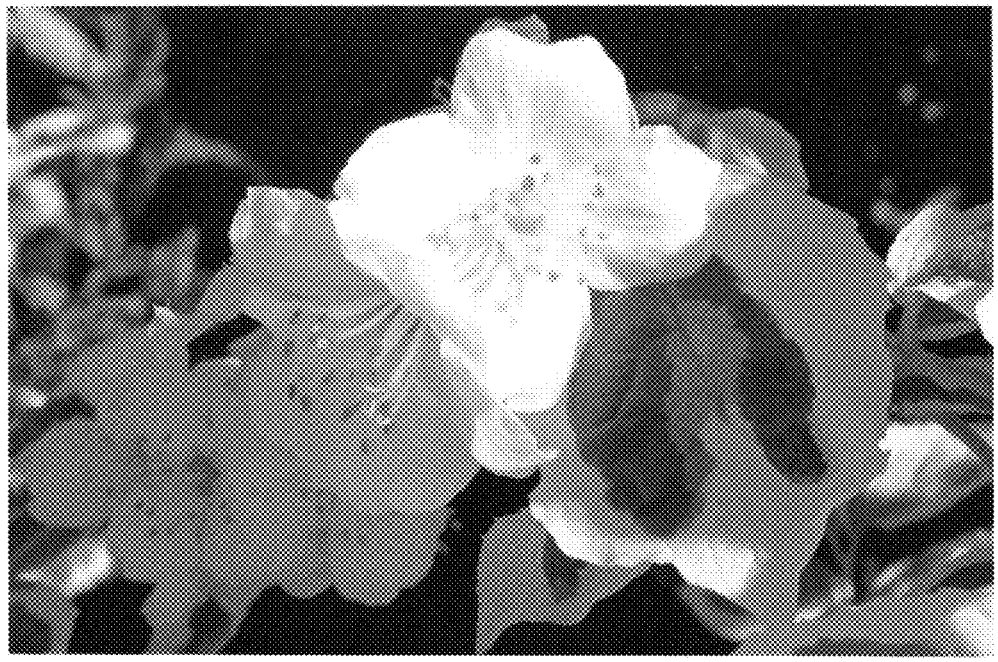

The photograph in FIG. 2 provides a close-up view of the flowers of 'Icezam'.

Figure 3:
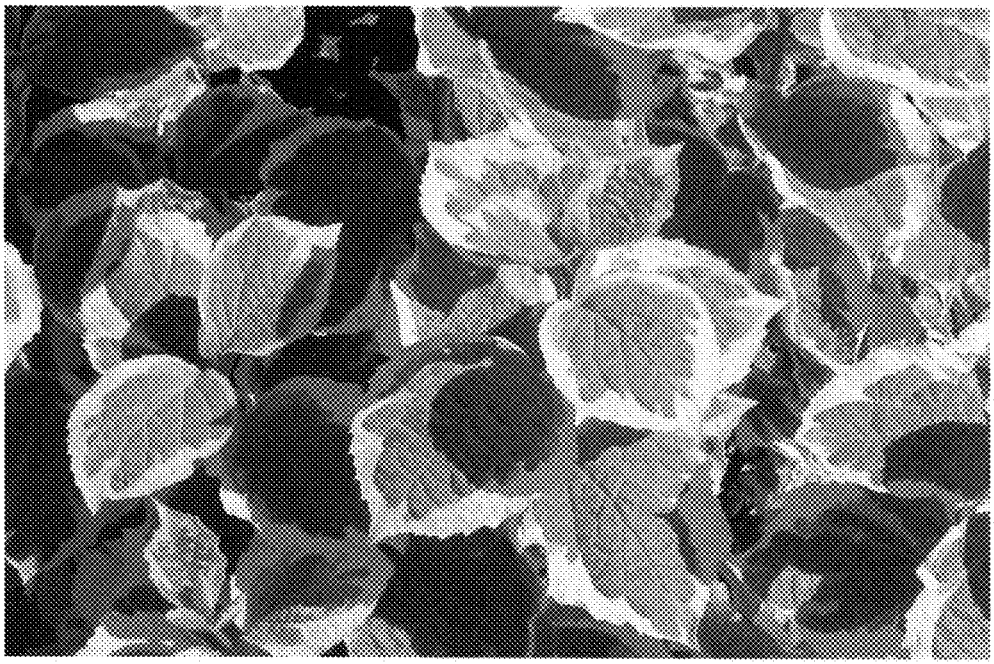

The photograph in FIG. 3 provides a close-up view of the foliage of 'Icezam'.

The colors in the photograph may differ slightly from the color values cited in the detailed botanical description, which accurately describe the colors of the new *Philadelphus*.

DETAILED BOTANICAL DESCRIPTION

The following is a detailed description of 2 year-old plants of the new cultivar as grown outdoors in full sun in a trial plot in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms for 2 to 3 weeks in late May to early June in Ohio.

*Plant type*.—Deciduous shrub.

*Plant habit*.—Upright and rounded.

*Plant size*.—Reaches about 1.8 to 2.4 m (6 to 8 feet) in height and width in four years in the landscape.

*Cold hardiness*.—At least to U.S.D.A. Zones 5.

*Diseases and pests*.—No susceptibility or resistance to diseases or pests has been observed.

*Root description*.—Fibrous, moderately dense.

*Propagation*.—Softwood stem cuttings.

*Growth rate*.—Moderately vigorous, slower than is typical of plants of *Philadelphus coronaria* with non-variegated leaves.

*Root development*.—Roots initiate in about 2 weeks, rooted cutting fully develop in a 2.5 inch container in about 60 days.

Stem description:

*Shape*.—Oval.

*Stem color*.—New growth; 144D, mature wood; a blend of N199B and 199D.

*Stem size*.—Basal branches; an average of 30 cm in length and 3 mm in diameter, lateral branches; an average of 30 cm in length and 3 mm in diameter.

*Stem surface*.—New growth; matte and sparsely covered with wooly hairs average of 1 mm in length and match the surface color, mature wood; slightly exfoliating (shreddy) at base, smooth and matte above base.

*Stem aspect*.—Upright to outward at an average angle of 40°.

*Branching*.—Basal and lateral branching, an average of 7 lateral branches per main stem, branch internode length; an average of 5 cm.

Foliage description:

*Leaf shape*.—Ovate to broadly elliptic.

*Leaf division*.—Simple.

*Leaf base*.—Rounded to slightly cordate.

*Leaf apex*.—Cuspidate.

*Leaf fragrance*.—None.

*Leaf venation*.—Primarily pinnate, upper surface glabrous and matches leaf color, lower surface slightly glossy and moderately covered with wooly hairs 1 mm in length matching the leaf color.

*Leaf margins*.—Serrated.

*Leaf arrangement*.—Opposite.

*Leaf attachment*.—Petiolate.

*Leaf surface*.—Upper surface is glabrous, lower surface is slightly sheen.

*Leaf internode length*.—An average of 7 mm.

*Leaf size*.—An average of 6 cm in length and 4 cm in width.

*Leaf quantity*.—An average of 8 per lateral stem, 15 cm in length.

*Leaf color*.—Newly expanded leaves upper and lower surface; 144C, margins 8A, mature leaves upper surface; 144A, margins 8C, mature leaves lower surface; centers 146B and margins 8C.

*Petioles*.—About 1 cm in length and 2 mm in width, color 146B, sparsely covered with short soft hairs 1 mm in length matching surface color.

Stipules: None.

Inflorescence description:

*Inflorescence type*.—Most typically is short racemes of 4 to 8 single flowers on upper axils, in pairs or single.

*Inflorescence size*.—Raceme is an average of 7 cm in diameter and 4.5 cm in depth.

*Flower buds*.—Globose in shape, an average of 8 mm in depth and 6 mm in diameter, NN155A in color with base matching sepal color.

*Flower fragrance*.—Slightly sweet, less fragrant than is typical of plants of *Philadelphus coronarius*.

*Lastingness of flowers*.—About 6 days.

*Flower aspect*.—Outward to upright.

*Flower quantity*.—An average of 4 inflorescences per lateral stem.

*Flower type*.—Rotate.

*Flower size*.—Average of 3.5 cm in diameter and 1.3 cm in depth.

*Peduncles*.—Average of 5.5 cm in length (when 6-flowered) and 1.5 mm in diameter, color 144D, glabrous surface, oval in shape.

*Pedicels*.—None, sessile to peduncle. There are on mine: Average of 3 mm in length and 1 mm in diameter, color 144D, glabrous surface, oval in shape.

*Calyx*.—Rotate in shape with lower portion fused, an average of 7 mm in depth and 1.5 cm in width (including tube portion),

*Sepals*.—4, ovate in shape, mucronate apex, fused at base (lower portion into tube), entire margin, free portion; an average of 6 mm in length and 4 mm in width, color on upper and lower surface when opening and mature a blend of 145C and 157C, color on lower surface when opening and mature, surface is glabrous on both surfaces.

*Petals*.—4, un-fused, broadly elliptic in shape, margin slightly undulated, apex rounded with notch, an average of 1.6 cm in length and width, outer and inner surface is glabrous, color of inner surface when opening and mature; NN155B, color of outer surface when opening and mature; NN155B.

Reproductive organs:

*Gynoecium*.—4 pistils, united, about 1 cm in length, style is an average of 0.9 cm in length, and N155B in color, stigma is 161C in color, ovary is inferior and surrounded by nectar secreting disk; 145 C in color, 4 mm in diameter and 6 mm in length.

*Androcoecium*.—About 20 stamens, filaments are N155B in color and an average of 1 cm in length, anthers are 160B in color, an average of 3 mm in length, basifixed and oblong in shape, pollen is moderate in quantity and 9A in color.

*Fruit and seed*.—Fruit; 4-valved capsule, about 7 mm in length and width, dries to 199B in color, seed: none observed.

It is claimed:

1. A new and distinct cultivar of *Philadelphus* plant named 'Icezam' as herein illustrated and described.

* * * * *